United States Patent
Sheftel et al.

(10) Patent No.: US 10,279,176 B1
(45) Date of Patent: *May 7, 2019

(54) METHOD AND APPARATUS FOR INCREASING ABSORPTION OF MEDICATIONS AND COSMECEUTICALS THROUGH THE SKIN OF THE USER

(71) Applicants: Scott N. Sheftel, Tucson, AZ (US); Jeffry B. Skiba, Chandler, AZ (US)

(72) Inventors: Scott N. Sheftel, Tucson, AZ (US); Jeffry B. Skiba, Chandler, AZ (US)

(73) Assignee: FIRST STEP HOLDINGS, LLC, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/005,436

(22) Filed: Jun. 11, 2018

(51) Int. Cl.
*A61N 1/32* (2006.01)
*A61N 1/04* (2006.01)
*A61N 1/20* (2006.01)
*A61K 9/00* (2006.01)

(52) U.S. Cl.
CPC ........ *A61N 1/325* (2013.01); *A61N 1/0428* (2013.01); *A61K 9/0014* (2013.01); *A61N 1/205* (2013.01)

(58) Field of Classification Search
None
See application file for complete search history.

(56) References Cited

U.S. PATENT DOCUMENTS

| | | | |
|---|---|---|---|
| 4,425,917 A | 1/1984 | Kuznetz | 607/110 |
| 5,445,901 A | 8/1995 | Korall et al. | 429/27 |
| 5,861,044 A | 1/1999 | Crenshaw | 8/115 |
| 6,602,811 B1 | 8/2003 | Rock et al. | 442/312 |
| 8,204,587 B2 | 6/2012 | Pak et al. | 604/20 |
| 9,192,761 B2 | 11/2015 | Sheftel et al. | A61N 1/32 |
| 9,707,172 B2 | 7/2017 | Sheftel et al. | A61K 9/0009 |
| 2002/0086036 A1 | 7/2002 | Walker | 424/236.1 |
| 2005/0010192 A1 | 1/2005 | Sun et al. | 604/501 |
| 2007/0191756 A1 | 8/2007 | Tapper | 604/20 |
| 2010/0082088 A1* | 4/2010 | Fassih | A61K 9/0009 607/149 |
| 2010/0209515 A1 | 8/2010 | Chantalat et al. | 424/490 |
| 2012/0016446 A1 | 1/2012 | Panting | 607/62 |
| 2012/0064313 A1 | 3/2012 | Rock et al. | 428/212 |
| 2016/0008273 A1* | 1/2016 | Sheftel | A61K 9/0009 424/402 |

FOREIGN PATENT DOCUMENTS

| | | | |
|---|---|---|---|
| EP | 0 364 153 | 4/1990 | B01J 35/06 |
| WO | WO2010027792 | 3/2010 | A61N 1/20 |

OTHER PUBLICATIONS

U.S. Appl. No. 14/213,735, filed Mar. 14, 2014.
U.S. Appl. No. 14/864,541, filed Sep. 24, 2015.
U.S. Appl. No. 15/823,076, filed Nov. 27, 2017.
Anonymous, "Micro Current Technology," downloaded Feb. 10, 2015 from http://www.bio-therapeutic.in/micro-current-technology.php (5 pgs).

(Continued)

*Primary Examiner* — Imani N Hayman
*Assistant Examiner* — Tiffany Legette
(74) *Attorney, Agent, or Firm* — Hayes Soloway P.C.

(57) ABSTRACT

A self-contained "battery-free" iontophoresis apparatus and method are provided.

19 Claims, 1 Drawing Sheet

(56) References Cited

OTHER PUBLICATIONS

Anonymous, "Microcurrent Stimulation and Microcurrent Therapy," downloaded Feb. 10, 2015, from http://www.microcurrentsystems.com ) (5 pgs).

Anonymous, "Ohm's Law (again!)," Electrical Safety-Electronics Textbook, downloaded Mar. 8, 2015 from http://www.allaboutcircuits.com/vol_1/chpt-3/4.html (6 pgs).

Bagherani et al., "An overview of zinc and its importance in dermatology—Part II: The association of zinc with some dermatologic disorders", Separtment of Dermatology, University of Rochester, School of Medicine and Dentistry USA, Glob Dermatol, 2016, vol. 5(5), pp. 337-350.

Bogie et al., "Effects of regular use of neuromuscular electrical stimulation on tissue health," Journal of Rehabilitation Research and Development. vol. 40, No. 6, Nov./Dec. 2003, pp. 469-476 (7 pgs).

Bolton et al., "Direct-Current Bactericidal Effect on Intact Skin," Antimicrobial Agents and Chemotherapy, Jul. 1980, pp. 137-141 (5 pgs).

Bruning, Elizabeth, "A new topical product form featuring biomimetic electrical signaling generated by a zinc-copper galvanic couple improves the signs of clinical photoaging in a 12-week placebo-controlled study", Journal of the American Academy of Dermatology, vol. 66, issue 4, Supplement 1, p. AB31.

Camel et al., "The Effect of Saline Iontophoresis on Skin Integrity in Human Volunteers," Fundamental and Applied Toxicology 32, 168-178 (1996) (11 pgs).

Carter et al., "Electric current flow through human skin at power frequency voltages," Brit. J. Industr. Med., 1969, 26, pp. 217-233 (7 pgs).

Chandak et al., "Modern Homeopathy An evidence based information on Homoeopathy," website: http://www.modernhomeopathy.com/anndt%20law.htm as of Oct. 8, 2015 (2 pgs).

Cheng et al., "The Effects of Electric Currents on ATP Generation, Protein Synthesis, and Membrane Transport in Rat Skin," Clinical Orthopaedics and Related Research, 171, (Nov.-Dec. 1982) pp. 264-272 (9 pgs).

Cole, K.S., "Electrical Conductance of Biological Systems," Cold Spring Harbor Symposia on Quantitative Biology, 1933, 1:107-116 (excerpt only) (1 pg).

Fish et al., *Medical and Bioengineering Aspects of Electrical Injuries*, Lawyers & Judges Publishing Company, 2003, book overview (13 pgs).

Giudice, "Reinforcement Fibers in Zinc-Rich Nano Lithiun Silicate Anticorrosive Coatings", UTN (Universidad Technologica Nacional), Chapter 7, www.intechopen.com; 2012.

Guffey et al., "Skin pH changes associated with iontophoresis," J Orthop Sports Phys Ther., Nov. 1999; 29(11):656-60 (2 pgs).

Gupta et al., "Zinc Therapy in Dermatology: A Review"; Department of Dermatology, Venereology & Leprosy, Hindawi Publishing Corporation; vol. 2014, Article IDS 709152, 11 pages, Published Jul. 10, 2014.

International Preliminary Report on Patentability issued in application No. PCT/US2014/029239, dated Sep. 24, 2015 (8 pgs).

International Search Report and Written Opinion issued in application No. PCT/US2014/029239, dated Jul. 7, 2014 (10 pgs).

Kirsch et al., "Electromedicine: The Other Side of Physiology," Innovations in Pain Management: A Practical Guide for Clinicians (6th ed.) Boca Raton, Fla., 2002, American Academy of Pain Management, CRC Press, pp. 749-758 (14 pgs).

Ladizinsky, et al., "New Insights Into Oxygen Therapy for Wound Healing," Wounds, 2010, vol. 22, No. 12, pp. 294-300. (11 pgs).

Lambert et al., "Electro-membrane microcurrent therapy reduces signs and symptoms of muscle damage," Medicine & Science in Sports & Exercise, 2002, vol. 34, No. 4, pp. 602-607 (6 pgs).

Li et al., "A Method for Measuring the Volume of Transdermally Extracted Interstitial Fluid by a Three-Electrode Skin Resistance Sensor," Sensors, 2014, 14, 7084-7095 (12 pgs).

Ma et al., "Extraordinarily High Conductivity of Stretchable Fiberts of Polyurethane and Silver Nanoflowers", ACS Nano, 2015, 9(11), pp. 10876-10886.

Madehow.com, "Polyester"; vol. 2; accessed Oct. 3, 2017; http://www.madehow.com/Volume-2/Polyester.html.

McMakin, C., "Microcurrent therapy: a novel treatment method for chronic low back myofascial pain," Journal of Bodywork and Movement Therapies, 2004, 8, pp. 143-153 (11 pgs).

Miscellaneous, "Doctors' Comments," downloaded Oct. 8, 2015 from http://www.drionics.com (5 pgs).

Muirhead, "Antibacterial Ointments Versus Petrolatum-Based Ointments in Clean Wounds for Wound Healing", Pacific University CommonKnowledge, School of Physician Assistant Studies, Theses, Dissertations and Capstone Products; Aug. 11, 2012.

Notice of Allowance issued in U.S. Appl. No. 14/213,735, dated Jul. 24, 2015 (7 pgs).

Notice of Allowance issued in U.S. Appl. No. 14/864,541, dated Oct. 25, 2016 (10 pgs).

Nuttall et al., "Zinc and the aging brain", Genes Nutr (2014) 9:379, Jul. 16, 2013.

Office Action issued in U.S. Appl. No. 14/213,735, dated Apr. 17, 2015 (6 pgs).

Office Action issued in U.S. Appl. No. 14/213,735, dated Feb. 3, 2015 (10 pgs).

Office Action issued in U.S. Appl. No. 14/213,735, dated Jun. 19, 2015 (7 pgs).

Office Action issued in U.S. Appl. No. 14/213,735, dated Oct. 7, 2014 (13 pgs).

Office Action issued in U.S. Appl. No. 14/864,541, dated Jun. 6, 2016 (25 pgs).

Park et al., "The Effect of Microcurrent Electrical Stimulation on the Foot Blood Circulation and Pain of Diabetic Neuropathy," Journal of Physical Therapy Science, 2011, vol. 23, No. 3, pp. 515-518 (4 pgs).

Pfeiffer, E.A., "Electrical stimulation of sensory nerves with skin electrodes for research, diagnosis, communication and behavioral conditioning: a survey," Medical Biological Engineering, 1968, vol. 6, issue 6, pp. 637-651 (7 pgs).

Poltawski et al., Bioelectricity and microcurrent therapy for tissue healing—a narrative review, Physical Therapy Reviews, 2009, vol. 14, No. 2, pp. 105-114 (9 pgs).

Richter, C.P., "Physiological factors involved in the electrical resistance of the skin," American Journal of Physiology. vol. 88, 1929, pp. 596-615 (abstract only) (1 pg).

Rowlerson et al., "The fibre-type composition of the first branchial arch muscles in carnivore and primates," Journal of Muscle Research & Cell Motility Aug. 1983, vol. 4, issue 4, pp. 443-472 (5 pgs).

Shanmuganathan et al., "Highly Stretchable Thermoset Fibers and Nonwovens Using Thiol-ene Photopolymerization", ACS Applied Materials and Interfaces, 2014 6(16) pp. 14259-14265.

Suzuki, D., "The Body Electric," Skin Inc., Oct. 2007, downloaded from http://www.skininccom/skinscience/physiology/17969919.html (6 pgs).

Wang, W., "Oxygen partial pressure in outer layers of skin: simulation using three-dimensional multilayered models," Microcirculation, Mar. 2005, vol. 12, No. 2, pp. 195-207 (abstract only) (2 pgs).

Wikipedia, Heatsetting; accessed Oct. 3, 2017, https://en.wikipedia.org/wiki/heatsetting.

Wikipedia, Metal-Air electrochemical cell; accessed Oct. 2, 2017, https://en.wikipedia.org/wiki/metal%E2%80%93_air_electrochemical_cell.

Wikipedia, Nonwoven fabric; accessed Oct. 2, 2017, https://en.wikipeda,org/wiki/nonwoven_fabric.

* cited by examiner

METHOD AND APPARATUS FOR INCREASING ABSORPTION OF MEDICATIONS AND COSMECEUTICALS THROUGH THE SKIN OF THE USER

BACKGROUND OF THE INVENTION

The present invention relates to a method and apparatus for increasing absorption of substances through the skin of the user. The invention has particular utility in connection with increasing absorption of medications through the skin, and will be described in connection with such utility, although other utilities, such as increasing the speed or depth of absorption of other substances including, for example, cosmeceuticals, is contemplated.

Skin comprises epidermis, dermis, and subcutaneous adipose tissue. When medicines are applied to the skin, the epidermis, i.e., the upper layer of the skin, ordinarily considers the medicines as foreign substances and hinders absorption of the medicine. As a result, due to the influence of molecular size, bio characteristics, biochemical phenomena, and the like, the amount of medicines practically absorbed into the skin is very small.

In order to overcome this problem, iontophoresis has been developed to increase absorption of medicines through the skin. Iontophoresis involves generating a micro current to flow through the skin thereby effectively increasing absorption of components contained in the medicines having electrical affinity with the skin, by electrical repulsive force. Iontophoresis may be used, for example, so that topical vitamin C, which is an anti-oxidant and a co-factor in skin growth, is absorbed into the skin providing cellular stimulation and anti-oxidant protection. Topical vitamin C is used for skin health and improvement of wrinkles. Other uses of iontophoresis can range from medication delivery, such as with prescription medications, to localized delivery without systemic side-effects.

Current iontophoresis apparatuses induce electric fields on and around the skin by attaching patches to the skin, and allowing micro current to flow from the patches into the skin. However, current iontophoresis apparatuses require a source of electricity, e.g. a battery or connection to electrical mains, wires, circuits, etc., which are costly and bulky, and are inconvenient to use, resulting in reduced patient compliance. Thus a need exists for a self-contained, low cost method and apparatus for delivering medicines for absorption through the skin. In addition to the iontophoretic effect on the skin, directed electric micro current can also stimulate the skin, enhance blood flow and tissue oxygenation, as well as an enhance cellular response with increased protein synthesis, amino acid transport and increased ATP (mitochondrial energy) synthesis. The net effect is localized collagen stimulation addressing wrinkles, complexion and the health of the skin.

SUMMARY OF THE INVENTION

In our prior U.S. Pat. Nos. 9,192,761 and 9,707,172 we describe methods and devices for treating hyperhidrosis and other conditions such as neuropathic pain, peripheral artery disease and neuropathy; for surgical rehabilitation and surgical convalescence including joint surgery rehabilitation and soft tissue healing; and for physical therapy including muscle and tendon healing and stroke rehabilitation, by applying onto a skin surface of a patient in need of said treatment, a device comprising a fabric containing elemental zinc particles arranged so that the fabric forms a plurality of half-cells of an air-zinc battery, whereby to produce ion exchange with the skin of the patient. As described in our aforesaid patents, elemental zinc particles or particles of zinc salt against the skin will result in secondary reactions to form zinc complexes beneficial to the host. The ability to deliver topical zinc to the surface of the skin can have beneficial effects provided the topical zinc is in the correct elemental presentation, availability and configuration.

The unique therapeutic value of zinc, zinc oxide and zinc salt in cosmetic and medicinal ointments and creams, i.e., for treating a variety of skin conditions is well documented in the art.

Also, as reported in our pending U.S. application Ser. No. 15/823,076 many of the same benefits of direct application to the skin of creams or ointments containing zinc may be achieved by bringing a fabric having elemental zinc particles printed thereon, in contact with the skin of the patient, i.e., as described in our aforesaid '761 and '172 patents.

We have now found that metal particle carrying fabrics such as described in our aforesaid '761 and '172 patents and our aforesaid '076 pending application advantageously may be used as a half cell in an oxidation/reduction reaction in contact with the skin to produce an electric current that when directed into the skin alters skin membrane permeability, allowing substances such as pharmaceuticals to pass more easily into the skin. That is to say, an electric field produced by metal particle carrying fibers, in contact with the skin provides a field direction, i.e., negative in the ion fabric and positive in the tissue. As a result, substances on the fabric or skin may be absorbed into the skin towards a positive pull to the tissue of the patient, by electrical repulsive force, i.e., negative to positive attraction, similar to iontophoresis. Thus, the present invention in essence provides a self-contained external battery-free iontophoresis apparatus for driving substances such as pharmaceuticals into the skin of the wearer.

The present invention in one aspect provides a device for increasing absorption of substances through the skin of an animal or human, comprising: a fabric or substrate; metal particles disposed on or exposed through at least a portion of a surface of the fabric or substrate, as a plurality of lines or dots in a specific pattern that positions the metal particles in discrete electrically isolated locations separated by a distance, wherein the fabric or substrate is configured such that said metal particles contact a skin surface of the human or animal, wherein the plurality of spaced lines are substantially evenly spaced from one other; and a layer adapted to hold a substance; wherein said fabric or substrate forms a plurality of half-cells of an air-metal battery, for ion exchange with the skin of the human or animal whereupon a substance located between the device and the skin of the animal or human is driven into the skin by iontophoresis.

In one aspect, the patterns conform to blood circulation patterns and/or nerve or underlying muscle patterns of the human or animal.

In another aspect, the lines or dots are evenly spaced at spacings from 0.1 to 3 mm, preferably 0.2 to 2 mm, more preferably 0.3 to 1.5 mm, most preferably 0.5 to 1 mm.

In yet another aspect, the lines or dots of lines are 0.1 mm to 5 mm wide, preferably about 0.1 to 3 mm, more preferably 0.2 to 2 mm, even more preferably 0.3 to 1 mm, most preferably 0.4 to 0.5 mm.

In still yet another aspect, the patterns cover from about 10% to 90% of the surface of the fabric or substrate, preferably from about 15% to about 75%, more preferable from about 25% to about 50%, most preferably from about 30% to about 40%.

In a preferred aspect the metal particles comprise a metal, metal oxide or metal salt, preferably elemental zinc particles, zinc oxide particles, and zinc salt particles, or aluminum, iron, copper and magnesium, and an oxide or salt thereof.

In still yet another aspect, the device includes an adhesive or adhesive tabs adapted to fix the device to the skin of the animal or human. In the case where the device is fixed to the skin by an adhesive, the metal particles may be incorporated directly into the adhesive.

The present invention also provides a method for increasing absorption of a substance through the skin of a human or animal, comprising locating the substrate adjacent the skin of the human or animal; and disposing onto the skin of the human or animal over the substance, a device comprising: a fabric or substrate; metal particles disposed on at least a portion of a surface of the fabric or substrate, as a plurality of lines or dots in a specific pattern that positions the metal particles in discrete electrically isolated locations separated by a distance, wherein the fabric or substrate is configured such that said metal particles contact a skin surface of the human or animal, wherein the plurality of spaced lines are substantially evenly spaced from one other, wherein said fabric or substrate forms a plurality of half-cells of an air-metal battery, which alters skin membrane permeability and drives the substance into the skin.

In one aspect of the method, the patterns conform to blood circulation patterns and/or nerve or underlying muscle patterns of the human or animal.

In another aspect of the method, the lines or dots are evenly spaced at spacings from 0.1 to 3 mm, preferably 0.2 to 2 mm, more preferably 0.3 to 1.5 mm, most preferably 0.5 to 1 mm.

In yet another aspect of the method, the lines or dots of lines are 0.1 mm to 5 mm wide, preferably about 0.1 to 3 mm, more preferably 0.2 to 2 mm, even more preferably 0.3 to 1 mm, most preferably 0.4 to 0.5 mm.

In still yet another aspect of the method, the patterns cover from about 10% to 90% of the surface of the fabric or substrate, preferably from about 15% to about 75%, more preferable from about 25% to about 50%, most preferably from about 30% to about 40%.

In a preferred aspect of the method, the metal particles comprise a metal, metal oxide or metal salt, preferably elemental zinc particles, zinc oxide particles, and zinc salt particles, or aluminum, iron, copper and magnesium, and an oxide or salt thereof.

In still yet another aspect of the method, the device is fixed to the skin of the animal or human, using an adhesive or adhesive tabs. In the case where the device is fixed to the skin using an adhesive, the metal particles may be incorporated directly into the adhesive.

The present invention also provides a method for increasing absorption of a substance through the skin of a human or animal, comprising: disposing. the substance in contact with the skin of a human or animal; and covering the substance with a fabric device comprising: a fabric or substrate; metal particles disposed on at least a portion of a surface of the fabric or substrate, as a plurality of lines or dots in a specific pattern that positions the metal particles in discrete electrically isolated locations separated by a distance, wherein the fabric or substrate is configured such that said metal particles contact a skin surface of the human or animal, wherein the plurality of spaced lines are substantially evenly spaced from one other, wherein said fabric or substrate forms a plurality of half-cells of an air-metal battery with the skin of the human or animal, whereupon the metal particles in the fabric form a first half cell of a battery circuit, while the body of the human or animal forms a second half cell of the battery circuit with oxygen from the host, whereupon the substance is driven into the skin of the human or animal by iontophoresis.

In one aspect of the latter method, the patterns conform to blood circulation patterns and/or nerve or underlying muscle patterns of the human or animal. Alternatively, the patterns may also conform to meridians and the focal points of meridians as defined by Asian medicine.

In another aspect of the latter method, the lines or dots are evenly spaced at spacings from 0.1 to 3 mm, preferably 0.2 to 2 mm, more preferably 0.3 to 1.5 mm, most preferably 0.5 to 1 mm.

In yet another aspect of the latter method, the lines or dots of lines are 0.1 mm to 5 mm wide, preferably about 0.1 to 3 mm, more preferably 0.2 to 2 mm, even more preferably 0.3 to 1 mm, most preferably 0.4 to 0.5 mm.

In still yet another aspect of the latter method, the patterns cover from about 10% to 90% of the surface of the fabric or substrate, preferably from about 15% to about 75%, more preferable from about 25% to about 50%, most preferably from about 30% to about 40%.

In a preferred aspect of the latter method, the metal particles comprise a metal, metal oxide or metal salt, preferably elemental zinc particles, zinc oxide particles, and zinc salt particles, or aluminum, iron, copper and magnesium, and an oxide or salt thereof.

In still yet another aspect of the latter method, an adhesive or adhesive tabs are used adapted to fix the device to the skin of the animal or human.

BRIEF DESCRIPTION OF THE DRAWINGS

Further features and advantages of the present invention will be seen from the following detailed description, taken in conjunction with the accompanying drawings, wherein.

DETAILED DESCRIPTION OF THE INVENTION

In the following description, the term "metal particles" may include elemental metal particles of metals capable of forming metal-air electrochemical cells, and oxides and salts thereof. Preferred are zinc metal particles and oxides and salts thereof, although other metals and oxides and salts thereof may be used including aluminum, iron, copper, or magnesium.

The term "fibers" may comprise both natural and synthetic fibers, filaments and threads, although synthetic fibers are preferred, in particular, fibers formed of thermoplastic or thermosetting plastic materials, and/or adhesive-coated fibers.

Figure 1:
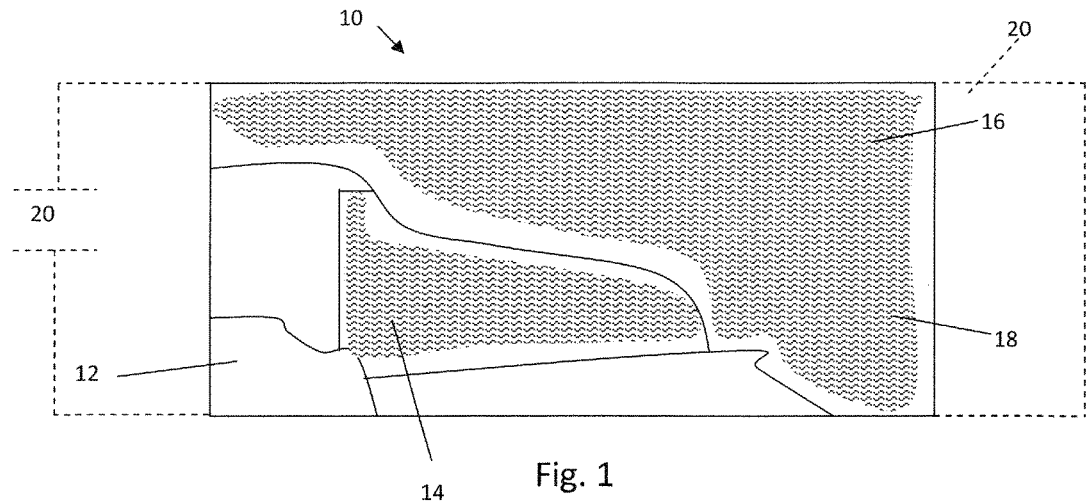
FIG. 1 is a top plan view, in partial a cross section, of a self-contained iontophoresis pad in accordance with the present invention.

Referring to FIG. 1, a self-contained, battery-free iontophoresis apparatus or device 10 in accordance with the present invention takes the form of a patch comprising a sandwich of a flexible substrate 12 formed of a sheet material such as an air permeable or non-air permeable textile or fabric which may include an adhesive-coated textile or fabric, a pharmaceutical carrier such as a gauze 14 and a cover 16 formed of a second sheet material carrying a plurality of spaced lines or lines of dots of metal particles, e.g. as described in our aforesaid '761 and '172 patents or as described in our '076 pending application. Preferably the metal particles are zinc particles and have an average particle size of between 1 and 100 nanometers, more preferably 1 to 10 microns, and even more preferably about 5 microns. The metal particles may be printed on the substrate 16, or extruded or melt spun at the time of fiber formation as taught by our aforesaid patents and pending application. Polyethylene is a material of choice for forming the fibers for releasing zinc ions. The amount of zinc and the surface area of the zinc or other metal used is a function of particle size and availability to create the battery. The amount of total zinc per unit volume will decide the capacity of the battery. When the zinc runs out the battery will also die out, unless there is recharging going on, e.g. due to ions present in the skin.

Preferably, but not necessarily, fabric 16 comprises a woven textile, although fabric 16 may be a non-woven textile, a fibrous mesh, a non-fibrous mesh, which may include an adhesive coated textile or fabric, mesh or the like.

Preferably, but not necessarily, opposite ends of the device 10 may include adhesive or adhesive tabs shown in phantom at 20 so that the iontophoresis device may be fixed to the skin of a user. Alternatively, the iontophoresis device 10 may be held in place by a wrap or the like.

As taught in our aforesaid '761 and '172 patents or as described in our '076 pending application, and as shown in FIG. 1, the metal particles are discontinuously and substantially uniformly distributed on the surface of fabric 16, in imaginary spaced lines or lines of dots, across the surface area of the fabric 16, at least in part. Typically, the lines or lines of dots are evenly spaced at spacings from 0.1 to 3 mm, preferably 0.2 to 2 mm, more preferably 0.3 to 1.5 mm, most preferably 0.5 to 1.0 mm. The concentration of metal such as zinc in the binder or in the extruded fibers that forms the lines or dots determines the amount of metal available for the "battery". Preferred concentration is 30% of the surface area of the fabric; however, the concentration of zinc may range from about 1% to about 99%. A mixture of binder and zinc metal may be formed as a paste and applied by silk screening e.g., as described in our aforesaid '761 and '172 patents. A 30% by weight zinc-to-binder is preferred for this. The line or dot width and length also determines the amount of metal in the deposition since the wider and longer the line, the more metal is available. Preferred line dots width is 1 mm width but width can vary from 0.1 mm up to 5 mm width. Since the deposition is on a fabric or carried in the adhesive, the amount of binder/metal applied also can be varied. In certain embodiments, the fabric being coated can be coated twice or more times over the same pattern whereupon the thickness of the deposition can be increased as desired. In certain embodiments, the metal deposition area patterns cover from about 10% to about 90% of the surface area of the fabric. In other embodiments, the metal deposition areas cover from about 20% to about 80%, from about 15% to about 75%, from about 25% to about 50%, or from about 30% to about 40% of the surface area of the fabric or anywhere in between. Although FIG. 1 shows the plurality of metal deposition areas 18 substantially uniformly distributed on the surface of the fabric, in other embodiments, the plurality of metal deposition areas may be randomly distributed on the surface of the fabric. Typically, the lines have a thickness of 0.1 to 3 mm, preferably 0.2 to 2 mm, more preferably 0.3 to 1.0, most preferably 0.4 to 0.5 mm. The spaced lines may be continuous and may take various forms including straight, curved and various angular shapes as shown, for example, straight continuous lines; straight broken lines; continuous saw-shaped; continuous wavy lines; broken wavy lines, etc, as described in our aforesaid '761 and '172 patents and our '076 pending application. The actual shape of the lines is not important. Preferably, but not necessarily, the lines are approximately equal in thickness and are evenly spaced.

Figure 2:
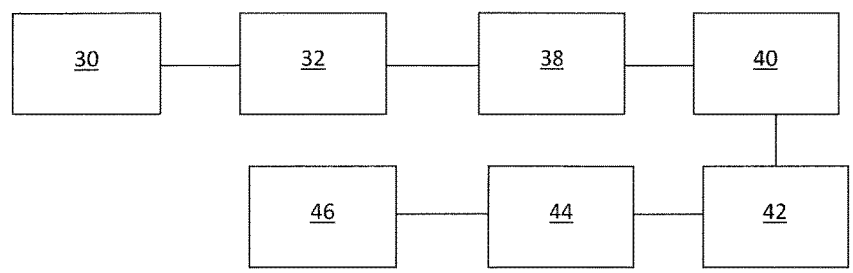
FIG. 2 is a flow chart diagrammatically illustrating a process for forming a self-contained iontophoresis pad in accordance with the present invention.
Figure 2A:
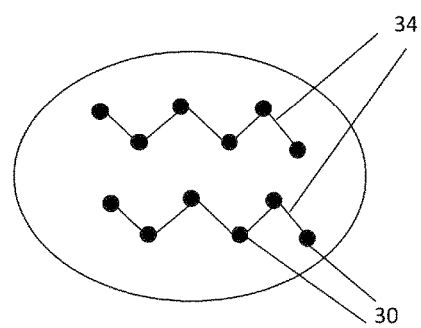
FIG. 2A is an enlarged view of an intermediate product formed by the process of FIG. 2.

Referring to FIGS. 2 and 2A, a self-contained external battery-free iontophoresis apparatus in accordance with the present invention is formed following the teachings of our aforesaid '076 application as follows: Metal particles, specifically elemental zinc particles, previously formed by grinding or precipitated out of suspension, and having an average particle size between 1 and 100 nanometers, more preferably 1-10 microns, even more preferably about 5 microns are mixed with a thermal plastic material such as polyethylene in a heated mixing vat 30 to melt the material, and the mixture extruded or melt spun at spinning station 32 to form fibers 34, having metal particles 36 contained therein. Polyethylene is the polymer of choice for releasing of electrons from the metal. The porosity of the fiber also is believed to play a part. Polyacrylic or polyester fibers also may be used however the result is a slower ion release. The metals containing fibers may then be cabled or twisted at a cabling station 38, and woven at a weaving or knitting station 40 into a sheet or cloth. The resulting metal particle impregnated sheet or cloth is cut to size at a cutting station 42, assembled together with a gauze pad impregnated with a medicine and a base sheet 12 as previously described at an assembly station 44, and the assembled package laminated together to form a self-contained battery-free iontophoresis apparatus at a laminating station 46. Lamination may be by application of glue on the border of base 12 and a metal-containing fabric 16, or by melt fusing the edges of the assembly.

There is thus provided a self-contained, external battery-free iontophoresis apparatus.

Various changes may be made in the above invention without departing from the spirit and scope thereof. For example, the amount of zinc in the fabric or adhesive coating can be increased or decreased to change the battery capacity. Adding too much zinc to a fiber may weaken the fiber so we can employ a bi-component concept where only the outside layer has the zinc and the inner core is polyester or another polymer that has more strength. By this method we can process the fiber differently than a polyethylene fiber loaded with zinc alone.

What is claimed:

1. A device for increasing absorption of substances through the skin of an animal or human, comprising, in order:
   a substrate layer;
   a treatment substance carrying layer holding a treatment substrate, carried on said substrate layer; and
   a cover layer disposed over said treatment substance carrying layer, said cover layer having metal particles disposed on or exposed through at least a portion of said cover layer as a plurality of lines or dots in a specific pattern that positions the metal particles in discrete electrically isolated locations separated by a distance, or disposed in or on an adhesive coating on said cover layer in a plurality of lines or dots in a specific pattern that positions the metal particles in discrete electrically isolated locations separated by a distance, wherein said cover layer is configured such that said metal particles are exposed at least in part, wherein said metal particles on said cover layer or carried by said adhesive coating form a plurality of half-cells of an air-or oxygen-metal battery, for ion exchange with the skin of the human or animal whereupon the treatment substance may be driven into the skin by iontophoresis.

2. The device of claim 1, wherein the patterns conform to blood circulation patterns and/or nerve or underlying muscle patterns of the human or animal.

3. The device of claim 1, wherein the lines or dots of lines are 0.1 mm to 5 mm wide, preferably about 0.1 to 3 mm, more preferably 0.2 to 2 mm, even more preferably 0.3 to 1 mm, most preferably 0.4 to 0.5 mm.

4. The device of claim 1, wherein the patterns cover from about 10% to 90% of the surface of the cover layer, preferably from about 15% to about 75%, more preferable from about 25% to about 50%, most preferably from about 30% to about 40%.

5. The device of claim 1, wherein the metal particles comprise a metal, metal oxide or metal salt.

6. The device of claim 1, wherein the metal particles are selected from the group consisting of elemental zinc particles, zinc oxide particles, and zinc salt particles.

7. The device of claim 1, wherein the metal particles are metal particles selected from the group consisting of aluminum, iron, copper and magnesium, and an oxide or salt thereof.

8. The device of claim 1, further including an adhesive pad or adhesive tabs adapted to fix the substrate layer.

9. The device of claim 1, wherein the lines or dots are substantially evenly spaced from one another.

10. The device of claim 9, wherein the lines or dots are evenly spaced at spacings from 0.1 to 3 mm, preferably 0.2 to 2 mm, more preferably 0.3 to 1.5 mm, most preferably 0.5 to 1 mm.

11. A method for increasing absorption of a substance through the skin of a human or animal, comprising:

providing a device as claimed in claim 1, and disposing the device in contact with the skin, of a human or animal, whereupon the metal particles form a first half cell of a battery circuit, while the body of the human or animal forms a second half cell of the battery circuit with oxygen, whereupon the substance is driven into the skin of the human or animal by iontophoresis.

12. The method of claim 11, wherein the patterns conform to blood circulation patterns and/or nerve or underlying muscle patterns of the human or animal.

13. The method of claim 11, wherein the lines or dots are evenly spaced at spacings from 0.1 to 3 mm, preferably 0.2 to 2 mm, more preferably 0.3 to 1.5 mm, most preferably 0.5 to 1 mm.

14. The method of claim 11, wherein the lines or dots of lines are 0.1 mm to 5 mm wide, preferably about 0.1 to 3 mm, more preferably 0.2 to 2 mm, even more preferably 0.3 to 1 mm, most preferably 0.4 to 0.5 mm.

15. The method of claim 11, wherein the patterns cover from about 10% to 90% of the surface of the cover layer, preferably from about 15% to about 75%, more preferable from about 25% to about 50%, most preferably from about 30% to about 40%.

16. The method of claim 11, wherein the metal particles comprise a metal, metal oxide or metal salt.

17. The method of claim 11, wherein the metal particles are selected from the group consisting of elemental zinc particles, zinc oxide particles, and zinc salt particles.

18. The method of claim 11, wherein the metal particles are metal particles selected from the group consisting of aluminum, iron, copper and magnesium, and an oxide or salt thereof.

19. The method of claim 11, further including fixing the device to the skin of the animal or human using adhesive.

\* \* \* \* \*